United States Patent
Nakamura et al.

(10) Patent No.: US 10,344,141 B2
(45) Date of Patent: Jul. 9, 2019

(54) BLACK IRON OXIDE FOR USE WITH COSMETICS, PRODUCTION METHOD THEREOF, AND COSMETIC MATERIALS COMPRISING THE SAME

(71) Applicant: TITAN KOGYO KABUSHIKI KAISHA, Ube-shi (JP)

(72) Inventors: Akira Nakamura; Masayasu Morishita, Yamaguchi (JP); Hiroaki Uchida, Yamaguchi (JP)

(73) Assignee: TITAN KOGYO KABUSHIKI KAISHA, Ube-shi (JP)

( * ) Notice: Subject to any disclaimer, the term of this patent is extended or adjusted under 35 U.S.C. 154(b) by 0 days.

(21) Appl. No.: 16/153,940

(22) Filed: Oct. 8, 2018

(65) Prior Publication Data

US 2019/0040227 A1 Feb. 7, 2019

Related U.S. Application Data

(62) Division of application No. 14/729,487, filed on Jun. 3, 2015, now Pat. No. 10,131,762.

(30) Foreign Application Priority Data

Jun. 11, 2014 (JP) ................. 2014-120261

(51) Int. Cl.
| | | |
|---|---|---|
| *C08K 3/22* | (2006.01) | |
| *A61K 8/19* | (2006.01) | |
| *A61K 8/25* | (2006.01) | |
| *A61K 8/26* | (2006.01) | |
| *A61Q 1/10* | (2006.01) | |
| *A61K 8/02* | (2006.01) | |
| *A61Q 1/02* | (2006.01) | |
| *C09C 1/24* | (2006.01) | |
| *C09C 3/06* | (2006.01) | |

(52) U.S. Cl.
CPC .............. *C08K 3/22* (2013.01); *A61K 8/0245* (2013.01); *A61K 8/19* (2013.01); *A61K 8/25* (2013.01); *A61K 8/26* (2013.01); *A61Q 1/02* (2013.01); *A61Q 1/10* (2013.01); *C09C 1/24* (2013.01); *A61K 2800/43* (2013.01); *A61K 2800/621* (2013.01); *A61K 2800/651* (2013.01); *C01P 2004/41* (2013.01); *C01P 2004/84* (2013.01); *C01P 2006/12* (2013.01); *C01P 2006/62* (2013.01); *C01P 2006/64* (2013.01); *C08K 2003/2227* (2013.01); *C08K 2003/2265* (2013.01); *C09C 3/063* (2013.01)

(58) Field of Classification Search
CPC .......... A61K 2800/43; A61K 2800/621; A61K 2800/651; A61K 8/0245; A61K 8/19; A61K 8/25; A61K 8/26; A61Q 1/02; A61Q 1/10; C08K 2003/2227; C08K 2003/2265; C08K 3/22; G01N 33/5079
See application file for complete search history.

(56) References Cited

U.S. PATENT DOCUMENTS

| | | |
|---|---|---|
| 5,470,660 A | 11/1995 | Misawa et al. |
| 6,420,030 B1 | 7/2002 | Hayashi et al. |
| 2002/0117084 A1 | 8/2002 | Hayashi et al. |
| 2005/0152828 A1* | 7/2005 | Aga .................. C01G 49/0018 423/594.2 |
| 2015/0361242 A1 | 12/2015 | Nakamura et al. |

FOREIGN PATENT DOCUMENTS

| | | | |
|---|---|---|---|
| EP | 0 825 235 A2 | 2/1998 | |
| EP | 0825235 | * 2/1998 | ............... C09C 1/00 |
| EP | 0 950 926 A2 | 10/1999 | |
| JP | 57-200230 | 12/1982 | |
| JP | 4-238819 | 8/1992 | |
| JP | 2000-327336 | 11/2000 | |
| JP | 2000-351629 A | 12/2000 | |
| JP | 2001-10821 A | 1/2001 | |
| JP | 2001-106529 A | 4/2001 | |
| JP | 2001-151512 A | 6/2001 | |
| JP | 2003-192352 A | 7/2003 | |
| JP | 2004-269355 A | 9/2004 | |
| JP | 1 849 839 A2 | 4/2007 | |
| JP | 2007-217320 | 8/2007 | |
| JP | 2007217320 | * 8/2007 | ............... A61K 8/19 |
| JP | 2007-314412 A | 12/2007 | |
| JP | 2011-213548 A | 10/2011 | |

OTHER PUBLICATIONS

Extended Search Report dated Nov. 3, 2015 in European Patent Application No. 15171334.4.
Office Action dated Jun. 27, 2017, issued in corresponding European Patent Application No. 15171334.4.
Carrick M. Eggleston et al., "The Structure of Hematite {001} Surfaces by Scanning Tunneling Microscopy; Image Interpretation, Surface Relaxation, and Step Structure," *American Mineralogist*, vol. 77, pp. 911-922 (1992).

* cited by examiner

*Primary Examiner* — Anna R Falkowitz
(74) *Attorney, Agent, or Firm* — Oblon, McClelland, Maier & Neustadt, L.L.P.

(57) ABSTRACT

To solve the problem of providing a black iron oxide that can yield sufficient blackness, opacifying effect and covering ability even if it is only added in a small amount for use with cosmetic materials, the invention provides a black iron oxide with a high tinting strength having an octahedral shape, a specific surface in a range of 8.0 to 20.0 m$^2$/g, and a particle surface coated with a layer containing one type or two or more types of inorganic compounds, wherein an L*value of a color on reduction is 31.0 or lower and a b*value of a color on reduction is 1.5 or lower, a production method thereof, and cosmetic materials that incorporate the same.

7 Claims, 2 Drawing Sheets

BLACK IRON OXIDE FOR USE WITH COSMETICS, PRODUCTION METHOD THEREOF, AND COSMETIC MATERIALS COMPRISING THE SAME

CROSS REFERENCE TO RELATED APPLICATIONS

This application is a division of U.S. application Ser. No. 14/729,487, filed Jun. 3, 2015, now allowed; and claims priority to Japanese Patent Application No. 2014-120261, filed Jun. 11, 2014, the disclosures of which are incorporated herein by reference in its entirety.

TECHNICAL FIELD

The present invention relates to a black iron oxide for cosmetics with a high tinting strength, a production method thereof, and a cosmetic material comprising black iron oxide.

BACKGROUND ART

Conventionally, black pigments are used in cosmetics for makeup of specific parts such as eyeliners. Those black pigments used for cosmetics which are commonly known are carbon black, black iron oxide, and titanium black, etc. Of these black pigments, carbon black and titanium black are approved as coloring materials in some countries, but not in others, and their use as materials for cosmetics in the global market are largely limited.

On the other hand, black iron oxide is safe, and it is used globally as a black pigment for cosmetics, but its tinting strength is lower than that of carbon black, and a large amount must be added to the cosmetics to obtain sufficient blackness, so it does not provide much degree of freedom in the recipe. Attempts are made to improve the tinting strength of black iron oxide to solve this problem.

One way of improving the tinting strength of black iron oxide is to reduce the grain size. One method that has been presented for reducing particle size is a method of forming bubbles of inert gas in an aqueous solution containing ferrous ion to reduce the dissolved oxygen content in the aqueous solution, then, adding an alkaline material to generate ferrous hydroxide, heating the solution to a range of 60 to 100° C., and producing a magnetite microcrystal (triiron tetroxide) having a particle size of 0.01 to 0.1 μm (Patent Document 1). However, a decrease in the grain size increases the surface area. As a result, there will be a higher possibility of oxidation of the surface of black iron oxide when contacting air at a high temperature, which leads to generation of maghemite that gives a reddish color. Patent Document 1 teaches that the black iron oxide needs to be vacuum dried to obtain a fine black iron oxide, but when drying is performed industrially under air, the particles turn brown. Hence, it is not practical to use black iron oxide as a black pigment for cosmetics.

In a conventional production of black iron oxide, a problem of color change by heat is experienced in the drying step during production, and a problem in heat resistance, such as thermochromism, is experienced during use. A production method has been proposed for producing magnetite particle powder for black pigments by adding a ferrous salt solution to an alkali hydroxide solution, passing oxidative gas over it at 80 to 100° C. and adding an aluminum compound, then subjecting the obtained magnetite particles to filtration, washing, drying, burning and pulverizing (Patent Document 2). The magnetite particles obtained by addition of aluminum taught in Patent Document 2 has an octahedral shape, their average particle size is 0.1 to 0.2 μm, and the specific surface is 20 $m^2/g$ to 50 $m^2/g$, but the tinting strength of the particles is not sufficient as black pigment. In Comparative Example 1, in which aluminum is not added, the specific surface was 11.3 $m^2/g$, but the color turned reddish brown, and black pigment was not obtained.

A proposal has also been made of a black iron tetroxide having a particle size of 100 nm or lower and a specific surface of 40 $m^2/g$ or higher, which is obtained by dropping a water-soluble ferrous salt solution into an alkali hydroxide or an alkali carbonate solution, blowing air into the solution to obtain a fine goethite precipitate (iron(II) oxyhydroxide), and hydrogenising the goethite precipitate at 250 to 350° C. (Patent Document 3). The black iron tetroxide of Patent Document 3 takes the form of needle shaped particles that do not easily disperse, and are lacking in tinting strength.

CITATION LIST

Patent Documents

[Patent Document 1] Japanese patent publication No. H04-238819
[Patent Document 2] Japanese patent publication No. 2000-327336
[Patent Document 3] Japanese patent publication No. S57-200230

SUMMARY OF INVENTION

Technical Problem

The object of the present invention is to provide a black iron oxide with a high tinting strength that can yield sufficient blackness, opacifying effect and covering ability even if it is only added in a small amount for use with cosmetic materials, a production method thereof, and cosmetic materials that incorporate a black iron oxide with a high tinting strength.

Solution to Problem

The present inventors performed extensive studies to develop a black iron oxide with a high tinting strength that can yield sufficient blackness, opacifying effect and covering ability even if it is only added in a small amount for use with cosmetic materials, and found that cosmetic materials incorporating the black iron oxide with a high tinting strength having an octahedral shape, a specific surface area in a range of 8.0 to 20.0 $m^2/g$, a particle surface coated with a layer containing one type or two or more types of inorganic compounds, and having a tinting strength indicated by an L*value of a colour on reduction of 31.0 or lower and a high blackness indicated by a b*value of a colour on reduction of 1.5 or lower, yields sufficient blackness, opacifying effect and covering ability even if it is only added in a small amount, wherein the L*value of a colour on reduction and the b*value of a colour on reduction are measured using a coated film made of a reduction paste comprising the black iron oxide particles of the present invention. The present invention was thus completed.

The black iron oxide of the present invention has an octahedral particle shape. The black iron oxide can also take the shape of a cube, an edgeless cube or a sphere, other than the octahedron, but the octahedron has the strongest tinting strength among those shapes. It is not clear why the tinting strength changes by the particle shape, but it is assumed that the good crystallinity of octahedron imparts a high light absorption efficiency and enhances the tinting strength. Further, good crystallinity causes improvement in heat resistance.

The index of the particle size of the black iron oxide of the present invention shown by the specific surface is in the range of 8.0 to 20.0 m$^2$/g. A black iron oxide having a high tinting strength indicated by an L*value of a colour on reduction that is 31.0 or lower cannot be obtained when the specific surface is lower than 8.0 m$^2$/g. Further, a specific surface that is higher than 20.0 m$^2$/g causes the b*value of the colour on reduction to be higher than 1.5, and thus makes the brownish color become more visible while blackness declines.

The particle surface of the black iron oxide of the present invention is coated with a layer containing one type or two or more types of inorganic compounds. An increase of the specific surface makes the black iron oxide more susceptible to oxidation, and imparts a brownish color tone to the particles while reducing blackness, but when the particle surface is coated with a layer containing one type or two or more types of inorganic compounds, the coating blocks the contact with oxygen in air and regulates oxidation in the drying step, so the brownish color is suppressed and the reduction of blackness is regulated. The inorganic compounds to coat the surface of the black iron oxide of the present invention may include hydroxides or oxides of metals, such as aluminum, silicon, zinc, titanium, zirconium, cerium and tin.

Advantageous Effects of Invention

The black iron oxide with a high tinting strength of the present invention has a higher tinting strength compared to conventional black iron oxides, so it can yield sufficient blackness, opacifying effect and covering ability even if it is only added in a small amount for use with cosmetic materials.

DESCRIPTION OF EMBODIMENTS

Detailed explanation is provided below of the black iron oxide with a high tinting strength of the present invention, a production method thereof, and cosmetic materials incorporating said black iron oxide.

The present invention relates to a black iron oxide with a high tinting strength having an octahedral shape, a specific surface in a range of 8.0 to 20.0 m$^2$/g, and a particle surface coated with a layer containing one type or two or more types of inorganic compounds, wherein an L*value of a colour on reduction is 31.0 or lower and a b*value of a colour on reduction is 1.5 or lower, a production method thereof, and cosmetic materials incorporating said iron oxide pigment.

Figure 1:
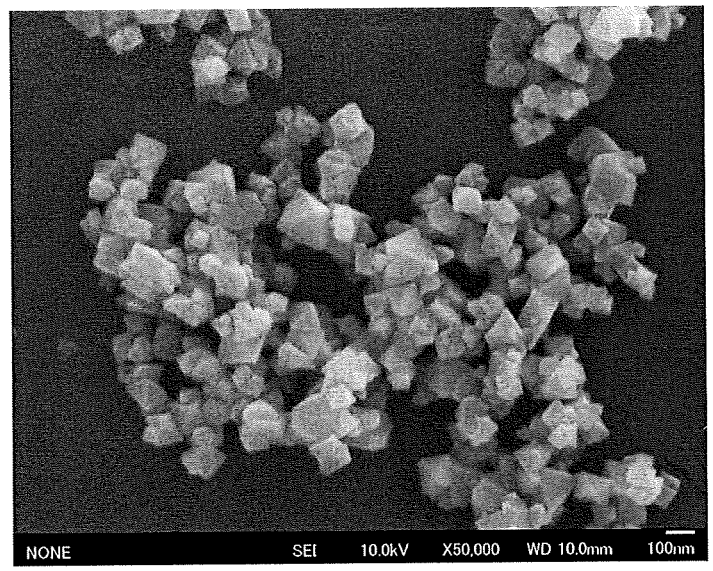
FIG. 1 is a scanning electron microscope (SEM) image showing the particle shape of the black iron oxide with a high tinting strength obtained in Example 1.

The particle shape of the black iron oxide of the present invention is the shape observed by a scanning electron microscope (SEM) image. As shown in FIG. 1, the particle shape of the black iron oxide of the present invention is a clear octahedral shape.

The specific surface of the black iron oxide of the present invention is a value measured by the single point BET method using Gemini 2360 (a product of Micromeritics) after deaeration of the sample in nitrogen at 150° C. for 30 minutes.

An L*value of the colour on reduction and a b*value of the colour on reduction of the black iron oxide of the present invention are color indices (L*value and b*value) shown according JIS Z 8781-4 based on values obtained by stirring 0.125 g of the sample, 0.375 g of titanium dioxide and 1.0 ml of styresol with a hoover muller to form a paste, adding 2.0 ml of styresol to the paste, then mulling and forming a paint from the mixture, coating a cast coat paper with the mixture using a 150 μm (6 mil) applicator to form a coated fragment (thickness of the film: about 30 μm), and air drying the fragment, followed by baking at 130° C. for 30 minutes, then measuring the color using a SM-7 type color tester by Suga Test Instruments. In addition, the "colour on reduction" is that according to the definition of the tinting strength of a pigment in JIS K5101-3-1 (Test methods for pigments—Part 3: Tinting strength—Section 1: Determination of relative tinting strength and colour on reduction of coloured pigments—Visual comparison method). Namely, "colour on reduction" means colour of reduction of a coated film made of a reduction paste, and "reduction paste" means paste obtained by mixing white pigment paste with colored pigment dispersed in a binder. In the present invention, the black iron oxide of the present invention corresponds to "colored pigment"

The L*value of the colour on reduction is an index of the tinting strength, and the smaller the L*value of the colour on reduction, the higher the tinting strength. The L*value of the colour on reduction of the conventional black iron oxide for cosmetics is about 38. An L*value of the colour on reduction of 31.0 or lower provides a sufficiently high tinting strength.

The b*value of the colour on reduction is an index of blackness, and a higher b*value of the colour on reduction makes the brownish color more visible and reduces blackness. When the b*value of the colour on reduction exceeds 1.5, the brownish color becomes too strong to be called black. When the b*value of the colour on reduction becomes a negative value, the blue color becomes strong, but a bluish black is also included in the scope of the present invention.

<Production Method of Black Iron Oxide with High Tinting Strength>

The production method of black iron oxide with a high tinting strength of the present invention is described in detail.

The ferrous salt solution was set to a predetermined temperature in the inert gas atmosphere, and an alkali solution at a neutralization equivalent or higher was added to the solution to generate a ferrous hydroxide slurry. Then, a predetermined amount of ferric salt solution is added to the ferrous hydroxide slurry to induce nucleation of black iron oxide. Subsequently, an alkali solution is added to the slurry containing nuclei of black iron oxide to adjust the pH of the slurry to a range of 12.0 to 13.0, and preferably, an oxygen-containing gas is passed over the slurry while it is heated to a range of 60 to 100° C. to induce the growth of the nucleus of black iron oxide. A predetermined amount of metal salt is added to the slurry after generation of black iron oxide has ended, and the pH of the mixture is adjusted by acid or alkali to obtain an insoluble hydroxide of the metal salt to be deposited onto the particle surface of the black iron oxide. Then, the slurry containing black iron oxide coated with an inorganic compound is filtered out, washed to remove salt impurities, and subsequently dried to obtain black iron oxide particles coated with an inorganic compound, preferably an inorganic metal hydroxide or oxide, of the present invention.

The ferrous salts used in the present invention include ferrous chloride, ferrous sulfate, and ferrous nitrate. In addition, hydroxides such as sodium hydroxide, potassium hydroxide, and ammonium hydroxide, carbonates such as sodium carbonate, potassium carbonate, and ammonium carbonate, or ammonia gas can be used as the alkali source, but an alkali source that contains ammonia vaporizes at a high neutralization temperature, so hydroxides are preferable.

The ferric salt that can be used in the present invention includes ferric chloride, ferric sulfate, and ferric nitrate. The amount of ferric salt to be added is 0.8 to 5.0 wt % as $Fe^{3+}$ against 100 wt % of $Fe^{2+}$. When the amount of ferric salt to be added is too small, the specific surface of the black iron oxide becomes smaller than 8.0 $m^2/g$. On the other hand, when the amount of ferric salt to be added is too large, the specific surface becomes higher than 20.0 $m^2/g$.

When the pH of the slurry containing nucleus of black iron oxide is lower than 12.0, the black iron oxides will not grow sufficiently, and particles having an octahedral shape will not be formed. An octahedral shape is also obtained when the slurry pH is higher than 13.0, but such case requires more alkali to be used and is not economic. When the temperature for heating slurry containing nucleus of black iron oxide is lower than 60° C., crystals of materials that are not black iron oxide such as goethite are generated, and the tinting strength and blackness declines. The black iron oxide with a high tinting strength desired in the present invention can be obtained at a temperature above 100° C., but it is not economic.

The slurry after completing the generation of black iron oxide with a high tinting strength is coated with a layer of one type or two or more types of inorganic compounds on the particle surface to suppress the decline of blackness due to oxidation in the drying step. A predetermined amount of inorganic metal salt can be added to the slurry containing black iron oxide to transform the inorganic metal salt into an insoluble hydroxide, and this process allows the surface of the black iron oxide particle to be coated with an inorganic compound. The inorganic metal salt to be used in the present invention is not particularly limited as long as they can be formed into a hydroxide or oxide of metals, such as aluminum, silicon, zinc, titanium, zirconium, cerium and tin, but it is preferably sodium aluminate, aluminum sulfate, aluminum nitrate, aluminum chloride, sodium silicate, potassium silicate, silicon tetrachloride, zinc sulfate, zinc chloride, titanium sulfate, titanium tetrachloride, zirconium oxychloride, zirconium sulfate, zirconium nitrate, cerous chloride, cerium nitrate, cerium acetate, tin chloride, stannous sulfate, and sodium stannate.

The amount of inorganic metal salt to be added is desirably an amount that can form a coating of an inorganic compound, preferably a coating of metal hydroxides or oxides in an amount of 0.5 to 5.0 wt % against 100 wt % of black iron oxide. When the amount of inorganic compound to be coated is lower than 0.5 wt %, the black iron oxide particle is oxidized in the drying step, the color tone becomes brownish, and the decline in blackness cannot be regulated. When the amount of inorganic compound for coating exceeds 5.0 wt %, the proportion of back iron oxide decreases and the tinting strength decreases.

<Organic Surface Treatment>

The surface of the black metal oxide particles of the present invention can be made water repellent and/or oil repellent by an organic matter to improve the dispersion stability and durability in the dispersion medium in the production of cosmetics that incorporate the black iron oxide particle of the present invention. The organic matter used herein may include dimethylpolysiloxane, methylhydrogenpolysiloxane and other silicone compounds, silane coupling agents, aluminum coupling agents, titanium coupling agents, zirconium coupling agents and other coupling agents, perfluoroalkyl phosphate compounds and other fluorine compounds, hydrocarbon, lecithin, amino acid, polyethylene, wax or lauric acid, stearic acid, isostearic acid and other fatty acids.

<Cosmetic Material>

The present invention provides a cosmetic material, in which black iron oxide particles that are surface coated with an inorganic compound (black iron oxide with a high tinting strength) are added in a predetermined amount against the main component of the cosmetic material. The amount of black iron oxide with a high tinting strength to be added in the cosmetic material may be set freely according to the required characteristics of the various cosmetic materials, and preferably in a range of 0.01-50 wt %, more preferably in a range of 0.02-40 wt % against the cosmetic material.

<Inorganic Pigment and Organic Pigment that can be Combined for Use>

The cosmetic material of the present invention can be combined for use with various additive components used in common cosmetic materials, such as inorganic pigments, and organic pigments. Inorganic pigments that can be combined for use may include titanium oxide, zinc oxide, iron red, yellow iron oxide, ultramarine blue, iron blue, cerium oxide, talc, muscovite, synthetic mica, bronze mica, black mica, synthetic fluorphlogopite, titanium-mica, mica-like iron oxide, sericite, zeolite, kaoline, bentonite, clay, silica, silica anhydride, magnesium silicate, aluminum magnesium silicate, calcium silicate, barium sulfate, magnesium sulfate, calcium sulfate, calcium carbonate, magnesium carbonate, boron nitride, bismuth oxychloride, alumina, zirconium oxide, magnesium oxide, chromium oxide, calamine, hydroxyapatite and composites thereof. Likewise, organic pigments that can be combined for use include silicone powder, silicone elastic powder, polyurethane powder, cellulose powder, nylon powder, urethane powder, silk powder, PMMA powder, starch, polyethylene powder, polystyrene powder, tar dye, natural dye, metal soaps, such as zinc stearate and composites thereof.

<Components that can be Added>

Note that the cosmetic material of the present invention can incorporate components other than those above in quantitative and qualitative ranges that do not impair the effect of the present invention in view of the purpose of use. For example, oil-based components, dyes, pH adjustors, humectants, thickeners, surfactants, dispersants, stabilizers, colorants, preservatives, antioxidants, sequestering agents, astringents, extinguishing agents, UV absorbers, perfumes and the like can be added in a range that achieves the object of the present invention.

<Form of Cosmetic Materials>

The cosmetic material of the present invention can be produced by a known method, and it can be in any form including powder, solid powder, cream, emulsion, lotion, liquid oil, solid oil, paste. For example, it can be in the form of cosmetics for make-up, cosmetics for skin care, cosmetics for hair care and the like including makeup base, foundation, concealer, face powder, control color (makeup base), sun screen, lipstick, lip cream, eyeshadow, eye liner, mascara, cheek color, manicure, body powder, perfume powder, baby powder, solid soap, bath powder, peel-off mask, without being limited thereby.

EXAMPLES

The present invention is described in more detail by Examples shown below. The following examples are given merely to provide examples, and they do not limit the scope of the invention.

Production Example 1

A ferrous sulfate solution (2.15 L) containing 1.50 mol/L of $Fe^{2+}$ was added to a 1.67 mol/L NaOH solution (3.85 L) in an inert gas atmosphere to generate ferrous hydroxide. (The amount of sodium hydroxide to be used is 1.04 equivalent against $Fe^{2+}$.) Then, a ferric sulfate solution at 1.7 wt % as $Fe^{3+}$ against $Fe^{2+}$ was added to the aqueous solution containing ferrous hydroxide to generate a crystal nucleus of black iron oxide. Subsequently, a NaOH solution was added to a ferrous hydroxide slurry containing nucleus of black iron oxide to adjust the pH to 12.3. The ferrous hydroxide slurry containing the nucleus was mechanically stirred at 90° C., then 2 L/min. of air was passed over for 120 minutes to induce growth of black iron oxide particles. Next, sodium aluminate at 1.5 wt % as $Al_2O_3$ was added slowly to the obtained black iron oxide while the mixture was stirred, and after 1 hour of stirring, diluted sulfuric acid was added to adjust the pH to 8.0. The mixture was filtered and washed, then dried at 100° C. to obtain Sample A. The scanning electron microscope (SEM) image of Sample A is shown in FIG. 1. As shown in FIG. 1, the particle shape of the obtained Sample A is an octahedron. The specific surface of Sample A measured by the BET method was 13.3 $m^2/g$. Further, the L*value of the colour on reduction of Sample A is 27.4, and the b*value of the colour on reduction is −1.1.

Production Example 2

A ferrous sulfate solution (2.15 L) containing 1.50 mol/L of $Fe^{2+}$ was added to a 1.67 mol/L NaOH solution (3.85 L) in an inert gas atmosphere to generate ferrous hydroxide. (The amount of sodium hydroxide to be used is 1.04 equivalent against $Fe^{2+}$.) Then, a ferric sulfate solution at 4.2 wt % as $Fe^{3+}$ against $Fe^{2+}$ was added to the aqueous solution containing ferrous hydroxide to induce nucleation of black iron oxide. Subsequently, a NaOH solution was added to a ferrous hydroxide slurry containing nucleus of black iron oxide to adjust the pH to 12.5. The ferrous hydroxide slurry containing the nucleus was mechanically stirred at 85° C., then 2 L/min. of air was passed over for 120 minutes to induce growth of black iron oxide particles. Next, sodium aluminate at 3.0 wt % as $Al_2O_3$ was added to the obtained black iron oxide slowly while the mixture was stirred, and after 1 hour of stirring, diluted sulfuric acid was added to adjust the pH to 8.0. The mixture was filtered and washed, then dried at 100° C. to obtain Sample B. The particle shape of the obtained Sample B is an octahedron, and the specific surface of Sample B measured by the BET method was 18.8 $m^2/g$. Further, the L*value of the colour on reduction of Sample B was 27.7, and the b*value of the colour on reduction was 1.1.

Production Example 3

A ferrous sulfate solution (2.15 L) containing 1.50 mol/L of $Fe^{2+}$ was added to a 1.67 mol/L NaOH solution (3.85 L) in an inert gas atmosphere to generate ferrous hydroxide. (The amount of sodium hydroxide to be used is 1.04 equivalent against $Fe^{2+}$.) Then, a ferric chloride solution at 0.9 wt % as $Fe^{3+}$ against $Fe^{2+}$ was added to the aqueous solution containing ferrous hydroxide to induce nucleation of black iron oxide. Subsequently, a NaOH solution was added to a ferrous hydroxide slurry containing nucleus of black iron oxide to adjust the pH to 12.1. The ferrous hydroxide slurry containing the nucleus was mechanically stirred at 95° C., then 2 L/min. of air was passed over for 120 minutes to induce growth of black iron oxide particles. Next, sodium aluminate at 1.5 wt % as $Al_2O_3$ was added slowly to the obtained black iron oxide while the mixture was stirred, and after 1 hour of stirring, diluted sulfuric acid was added to adjust the pH to 8.0. The mixture was filtered and washed, then dried at 100° C. to obtain Sample C. The particle shape of Sample C is an octahedron, and the specific surface of Sample C measured by the BET method was 8.6 $m^2/g$. Further, the L*value of the colour on reduction of Sample C was 28.8, and the b*value of the colour on reduction was −2.9.

Production Example 4

A ferrous sulfate solution (2.15 L) containing 1.50 mol/L of $Fe^{2+}$ was added to a 1.67 mol/L NaOH solution (3.85 L) in an inert gas atmosphere to generate ferrous hydroxide. (The amount of sodium hydroxide to be used is 1.04 equivalent against $Fe^{2+}$.) Then, a ferric sulfate solution at 1.7 wt % as $Fe^{3+}$ against $Fe^{2+}$ was added to the aqueous solution containing ferrous hydroxide to induce nucleation of black iron oxide. Subsequently, a NaOH solution was added to a ferrous hydroxide slurry containing nucleus of black iron oxide to adjust the pH to 12.7. The ferrous hydroxide slurry containing the nuclei was mechanically stirred at 80° C., then 2 L/min. of air was passed over for 120 minutes to induce growth of black iron oxide particles. Next, sodium silicate at 3.0 wt % as $SiO_2$ was added slowly to the obtained black iron oxide while the mixture was stirred, and after 1 hour of stirring, diluted sulfuric acid was added to adjust the pH to 5.0. The mixture was filtered and washed, then dried at 100° C. to obtain Sample D. The particle shape of the obtained Sample D is an octahedron, and the specific surface of Sample D measured by the BET method was 13.0 $m^2/g$. Further, the L*value of the colour on reduction of Sample D was 27.5, and the b*value of the colour on reduction was −1.0.

Production Comparative Example 1

Figure 2:
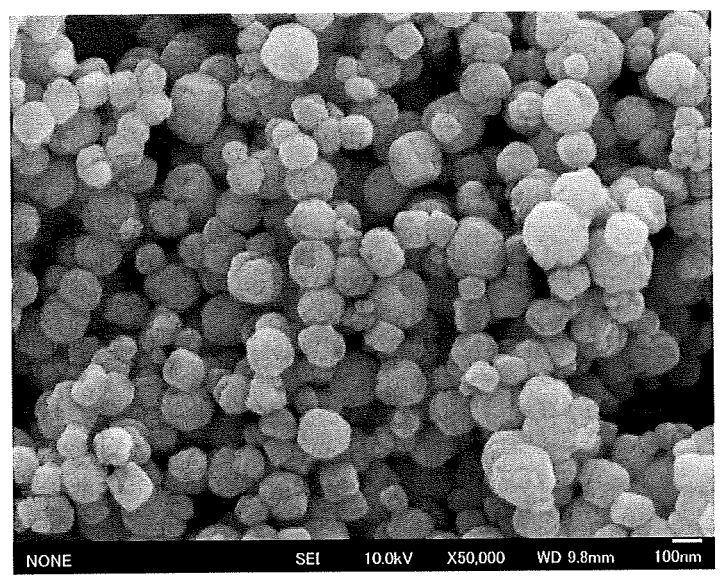
FIG. 2 is a SEM image showing the particle shape of the black iron oxide obtained in Comparative Example 1.

A process similar to Production Example 1, other than that the pH after nucleation was adjusted to 8.8, was performed to obtain Sample E. The scanning electron microscope (SEM) image of Sample E is shown in FIG. 2. As shown in FIG. 2, the particle shape is a sphere. The specific surface of Sample E was 12.0 $m^2/g$. Further, the L*value of the colour on reduction of Sample E was 31.5, and the b*value of the colour on reduction was −1.6.

Production Comparative Example 2

A process similar to Production Example 1, other than that a ferric sulfate solution was added at an amount of 0.7 wt % as $Fe^{3+}$ against $Fe^{2+}$, was performed to obtain Sample F. The particle shape of Sample F was an octahedron, and the specific surface was 7.5 m²/g. Further, the L*value of the colour on reduction of Sample F was 31.7, and the b*value of the colour on reduction was −3.4.

Production Comparative Example 3

A process similar to Production Example 1, other than adding a ferric sulfate solution at an amount of 7.0 wt % as $Fe^{3+}$ against $Fe^{2+}$, was performed to obtain Sample G. The particle shape of Sample G was an octahedron, and the specific surface was 22.0 m²/g. Further, the L*value of the colour on reduction of Sample G was 27.5, and the b*value of the colour on reduction was 2.4.

Production Comparative Example 4

A process similar to Production Example 1, other than that no surface treatment was performed after generating black iron oxide (addition of sodium aluminate), was performed to obtain Sample H. The particle shape of Sample H was an octahedron, and the specific surface was 13.1 m²/g. Further, the L*value of the colour on reduction of Sample H was 28.9, and the b*value of the colour on reduction was 1.7.

Figure 3:
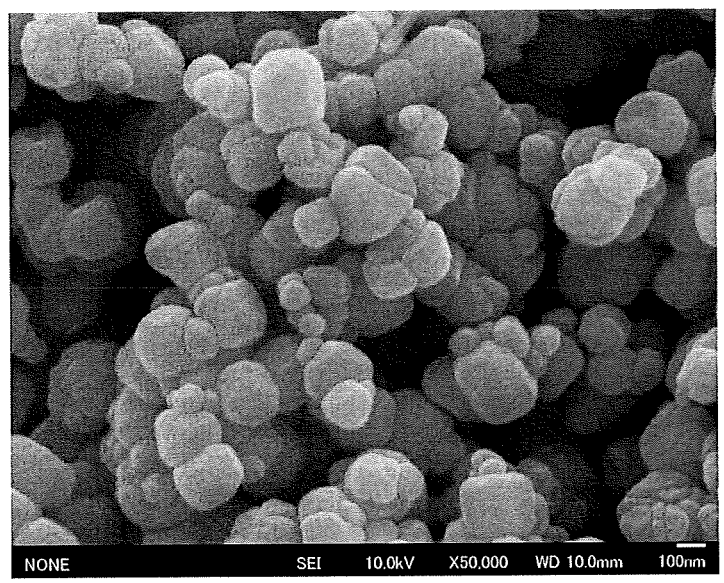
FIG. 3 is a SEM image showing the particle shape of a major black iron oxide, BL-100P (product of Titan Kogyo, Ltd.).

Examples 1-4, Comparative Examples 1-5: Pressed Eyeshadows 20.0 wt % of either of Samples A-D obtained in Production Examples 1-4 and Samples E-H obtained in Production Comparative Examples 1-5, and BL-100P produced by Titan Kogyo, Ltd. shown in the picture of FIG. 3 as a typical black iron oxide (particle shape: edgeless cube, specific surface 6.6 m²/g, L*value of the colour on reduction: 39.0, b*value of the colour on reduction: −4.2), 35.0 wt % of sericite, 14.9 wt % of talc, 20.0 wt % of titanium-mica (produced by BASF: Flamenco Super Pearl 120C) and 0.1 wt % of methylparaben were mixed/ground, and mixed. Then, 7.0 wt % of dimeticone 1000 cs (viscosity of 1000 mm²/s) and 3.0 wt % of diisostearyl malate that were mixed in a different container were added and stirred/mixed to homogenize the mixture. The mixture was dispersed in isopropyl alcohol to achieve a suitable viscosity, and pressed/filled in a gold plate having a diameter of 57 mm and a depth of 4 mm using a slurry filler. Then the mixture was dried at 40° C. for 12 hours to obtain the desired pressed eyeshadow.

[Assessment Items and Assessment Method Using Black Iron Oxide with a High Tinting Strength]

<Sensory Assessment>

The obtained pressed eyeshadow was subjected to a sensory assessment concerning the covering ability, blackness, gloss and the like.

<Assessment and Assessment Standard>

The pressed eyeshadows created in Examples 1-4 and Comparative Examples 1-5 were tested on 10 panels; a sensory assessment was performed by rating the sensory assessment items of Table 1 in a scale of 1 to 5; and the average score was used for judgment.

<Assessment Standard>

Very good: 5 Good: 4 Acceptable: 3 Not good: 2 Bad: 1

<Judgment Standard>

4.0-5.0 points: ⊚ 3.0-lower than 4.0 points: ○ 2.0-lower than 3.0 points: Δ 1.0-lower than 2.0 points: ×

The results are shown in Table 1.

TABLE 1

| | Ex. 1 | Ex. 2 | Ex. 3 | Ex. 4 | Comp. Ex. 1 | Comp. Ex. 2 | Comp. Ex. 3 | Comp. Ex. 4 | Comp. Ex. 5 |
|---|---|---|---|---|---|---|---|---|---|
| Applied black iron oxide | Sample A | Sample B | Sample C | Sample D | Sample E | Sample F | Sample G | Sample H | BL-100P |
| Test Items | | | | | | | | | |
| Covering ability | ⊚ | ⊚ | ○ | ⊚ | Δ | Δ | ⊚ | ⊚ | X |
| Blackness | ○ | ○ | ⊚ | ○ | ○ | ⊚ | X | X | ⊚ |
| Gloss | ⊚ | ○ | ⊚ | ⊚ | X | ○ | Δ | Δ | ○ |

As a result of the sensory assessment, the pressed eyeshadows obtained in Examples 1-5 of the present invention all had good covering ability and blackness, as well as gloss, compared to Comparative Examples 1-4 or Comparative Example 5, which incorporates a conventional black iron oxide. A cosmetic material that has good covering ability and blackness, and produces a glossy finish was obtained by incorporating a black iron oxide with high tinting strength having an octahedral shape, a specific surface in a range of 8.0 to 20.0 m²/g, a particle surface coated with a layer containing one or two or more types of inorganic compounds, and an L*value (colour on reduction) of 31.0 or lower and a b*value (colour on reduction) of 1.5 or lower.

Example 5: Aqueous Eyeliner

TABLE 2

| <Components> | Weight (%) |
|---|---|
| 1. Production Example 2 (Sample B) black iron oxide with high tinting strength | 7.0 |
| 2. Purified water | 21.5 |
| 3. Decaglyceryl laurate | 1.0 |
| 4. Glycerine | 6.0 |
| 5. Carboxymethyl cellulose 10% solution | 18.0 |
| 6. Phenoxyethanol | 0.5 |
| 7. Pentylene Glycol | 1.0 |
| 8. Vinyl acetate resin emulsion (Nisshin Chemical Industry Co., Ltd. Vinyblan GV-5651) | 45.0 |

<Production Method>

A: Components 1-3 were weighed out, and the black iron oxide was finely dispersed using a bead mill.

B: Components 4-7 were weighed out in a different container, and after A was added at 70° C. to the components and the mixture was dispersed homogenously, it was cooled to room temperature. Component 8 was added to obtain an aqueous eyeliner.

The obtained aqueous eyeliner had high blackness and opacifying effect.

Example 6: Emulsified Mascara

TABLE 3

| <Components> | Weight (%) |
| --- | --- |
| 1. Purified water | 23.1 |
| 2. Polyvinyl pyrrolidone | 2.0 |
| 3. Propanediol | 2.0 |
| 4. Cationized cellulose 1% solution | 10.0 |
| 5. Bentonite | 0.5 |
| 6. Triethanolamine | 1.7 |
| 7. Methylparaben | 0.2 |
| 8. Talc | 4.0 |
| 9. Production Example 2 (Sample B) black iron oxide with a high tinting strength | 10.0 |
| 10. Carnauba wax | 5.5 |
| 11. Beeswax | 9.0 |
| 12. Stearic acid | 2.0 |
| 13. Self-emulsifiable glyceryl stearate | 2.0 |
| 14. Propylene glycol stearate | 2.0 |
| 15. Hydrogenated polyisobutene | 2.0 |
| 16. Cyclomethicone | 4.0 |
| 17. Acrylate resin emulstion <Daito Kasei Kogyo Co. DAITOSOL 5000AD> | 20.0 |

<Production Method>
A: Components 8-10 were stirred/mixed using a Henschel mixer.
B: A was added to Components 1 to 7, and the mixture was dispersed homogenously using a stirrer.
C: After heated/dissolved Components 11-16 were added to B and emulsified, the mixture was cooled to 40° C., Component 17 was added, and the mixture was cooled to room temperature to obtain an emulsified mascara.

The obtained emulsified mascara was an emulsified mascara with a somewhat reddish blackness and a good opacifying effect.

Example 7: Eyebrow Pencil

TABLE 4

| <Components> | Weight (%) |
| --- | --- |
| 1. Production Example 4 (Sample D) black iron oxide with a high tinting strength | 20.0 |
| 2. Titanium oxide | 5.0 |
| 3. Talc | 10.0 |
| 4. Kaoline | 15.0 |
| 5. Japan wax | 21.0 |
| 6. Stearic acid | 10.0 |
| 7. Beeswax | 5.0 |
| 8. Hydrogenated castor oil | 5.0 |
| 9. Vaseline | 3.0 |
| 10. Lanolin | 3.0 |
| 11. Squalane | 3.0 |
| 12. Preservative | suitable amount |
| 13. Antioxidant | suitable amount |

<Production Method>
A: Components 1 to 4 were mixed/ground.
B: To heated/dissolved Components 5 to 13, A was added and the mixture was homogenously kneaded using a three roll mill.
C: The mixture was molded into a core and surrounded by wood into a pencil shape to obtain an eyebrow pencil.

The obtained eyebrow pencil had a smooth use, since it not only had high blackness, but it could also be added in a smaller amount.

Example 8: Cheek

TABLE 5

| <Components> | Weight (%) |
| --- | --- |
| 1. Triethoxycaprylylsilane-treated talc | 25.0 |
| 2. Triethoxycaprylylsilane-treated sericite | 61.0 |
| 3. Stearic acid treated titanium oxide particle (Titan Kogyo, Ltd. STV-455) | 3.0 |
| 4. Triethoxycaprylylsilane-treated titanium oxide | 2.0 |
| 5. Black iron oxide with a high tinting strength of Production Example 1 (Sample A) treated with triethoxycaprylylsilane at an amount of 1.5 wt % | 0.05 |
| 6. Triethoxycaprylylsilane-treated iron red | 0.15 |
| 7. Triethoxycaprylylsilane-treated yellow iron oxide | 0.8 |
| 8. Ethylhexyl methoxycinnamate | 3.0 |
| 9. Ethylhexyl palmitate | 5.0 |
| 10. Preservative | suitable amount |
| 11. Antioxidant | suitable amount |

<Production Method>
A: Components 1-7 were mixed using a Henschel mixer.
B: Components 8 to 11 were heated/dissolved and added to A, then it was ground with an atomizer.
C: The mixture was press-molded on an aluminum plate to obtain the desired check.

The obtained cheek had good usability.

Example 9: Nail Enamel

TABLE 6

| <Components> | Weight (%) |
| --- | --- |
| 1. Nitrocellulose (½ sec.) | 10.0 |
| 2. Modified alkyd resin | 10.0 |
| 3. Acetyl tributyl citrate | 5.0 |
| 4. Ethyl acetate | 20.0 |
| 5. Ethanol | 5.0 |
| 6. Toluene | 34.0 |
| 7. Production Example 2 (Sample B) black iron oxide with a high tinting strength | 3.0 |
| 8. Black iron oxide-coated titanium-mica (Timica Nu-Antique Silver by BASF) | 10.0 |
| 9. Organically modified montmorillonite | 3.0 |

<Production Method>
A: A half amount of each of Components 2, 3 was collected, and they were mixed with Components 7-8 and kneaded together.
B: Residue of Components 2, 3 and Components 1, 4-6 and 9 were added to A, and mixed until the mixture was homogenized to obtain nail enamel.

The obtained nail enamel had good blackness and opacifying effect.

Example 10: O/W Emulsified Foundation

TABLE 7

| <Components> | Weight (%) |
| --- | --- |
| 1. Stearic acid | 1.0 |
| 2. Isostearic acid | 0.3 |
| 3. Ethyl hexanoic acid cetyl | 4.0 |
| 4. Liquid paraffin 70cs | 11.0 |
| 5. Steareth-10 | 2.0 |
| 6. Cetyl alcohol | 1.5 |

TABLE 7-continued

| <Components> | Weight (%) |
|---|---|
| 7. Triethoxycaprylylsilane-treated talc | 5.0 |
| 8. Black Iron oxide with a high tinting strength of Production Example 3 (Sample C) treated with Triethoxycaprylylsilane at an amount of 1.0 wt % | 0.2 |
| 9. Triethoxycaprylylsilane-treated iron red | 0.3 |
| 10. Triethoxycaprylylsilane-treated yellow iron oxide | 1.8 |
| 11. Triethoxycaprylylsilane-treated titanium oxide | 8.0 |
| 12. Triethanolamine | 1.2 |
| 13. Propanediol | 5.0 |
| 14. Xanthan gum | 0.2 |
| 15. Purified water | 58.0 |
| 16. Phenoxyethanol | 0.5 |

<Production Method>
A: Components 7 to 11 were mixed/ground.
B: To Components 1 to 6 heated/dissolved at 85° C., A was added and the mixture was dispersed homogenously.
C: Components 12 to 16 were heated/dissolved at 85° C. and gradually added to B to obtain an emulsified mixture, and the mixture was stirred/cooled to room temperature to fill a suitable container and to obtain an O/W emulsifying foundation.

The obtained O/W emulsifying foundation spreads well, and it has a good covering ability as well as a fresh feel.

Example 11: Two-Way Cake Foundation

TABLE 8

| <Components> | Weight (%) |
|---|---|
| 1. Dimethicone-treated talc | residue |
| 2. Dimethicone-treated titanium oxide | 10.0 |
| 3. Dimethicone-treated mica | 20.0 |
| 4. Dimethicone-treated sericite | 36.0 |
| 5. Nylon powder | 10.0 |
| 6. Dimethicone-treated yellow iron oxide | 1.0 |
| 7. Dimethicone-treated iron red | 0.5 |
| 8. Black iron oxide with a high tinting strength of Production Example 4 (Sample D) treated with 1.0 wt % dimethicone | 0.1 |
| 9. Dimethicone 1000cs | 6.0 |
| 10. Isotridecyl isononanoate | 3.0 |
| 11. Squalane | 3.0 |
| 12. Tocopherol | 0.1 |
| 13. 1,3-Butylene glycol | 1.0 |

<Production Method>
A: Components 1-8 were mixed using a Henschel mixer.
B: Components 9 to 13 were heated/dissolved and added to A.
C: B was ground in an atomizer, and press-molded in an aluminum plate to obtain a two-way foundation.

The obtained two-way foundation had a smooth feel, and a fresh feel.

Example 12: Lipstick

TABLE 9

| <Components> | Weight (%) |
|---|---|
| 1. Ceresin | 10.0 |
| 2. Microcrystalline wax | 3.2 |
| 3. Paraffin | 5.0 |
| 4. Pentaerythrityl tetraisostearate | 20.0 |

TABLE 9-continued

| <Components> | Weight (%) |
|---|---|
| 5. Diisostearyl malate | 15.0 |
| 6. Hydrogenated polydecene | 10.0 |
| 7. Vaseline | 10.0 |
| 8. Polyglyceryl Triisostearate-2 | 22.1 |
| 9. Simethicone | 0.1 |
| 10. Propylparaben | 0.1 |
| 11. Red 202 | 0.6 |
| 12. Production Example 1 (Sample A) black iron oxide with a high tinting strength | 0.1 |
| 13. Titanium oxide | 0.4 |
| 14. Iron red | 0.4 |
| 15. Titanium-Mica (BASF: Flamenco Sparkle Gold 220J) | 2.0 |
| 16. Silica | 1.0 |

<Production Method>
A: Components 1-16 were weighed out, and heated/mixed.
B: A was dispersed evenly using a three roll mill, then it was further heated and stirred to a homogenous state.
C: After defoaming, a bulk of A was poured into a mold, and quenched. The bulk was fixed in a suitable container to obtain a lipstick.

The obtained lipstick exhibited a deep red color, and showed a unique color tone.

Example 13: Body Shampoo

TABLE 10

| <Components> | Weight (%) |
|---|---|
| 1. Lauric acid | 11.5 |
| 2. Myristic acid | 7.7 |
| 3. Palmitic acid | 4.8 |
| 4. Potassium hydroxide (48%) | 12.2 |
| 5. Lauryl hydroxy sulfo betaine | 10.0 |
| 6. Cocamide monoethanolamide | 1.0 |
| 7. Ethylene glycol distearate | 2.0 |
| 8. Purified water | 50.2 |
| 9. EDTA-4Na | 0.1 |
| 10. Production Example 1 (Sample A) black iron oxide with a high tinting strength | 0.1 |
| 11. Talc | 0.4 |

<Production Method>
A: Components 1 to 3 were heated/dissolved at 70 to 80° C.
B: Components 10 to 11 were mixed/ground.
C: Component 4 was added gradually to A to perform saponification. After saponification was completed, Components 5 to 9 were added, and the mixture was stirred until it reached a homogenous state.
D: C was cooled to 40° C., then B was added to it and the mixture was cooled to room temperature while it was being stirred/mixed to obtain a body shampoo.

The obtained body shampoo was colored with only a small amount of pigments, so pigments were prevented from precipitating under a high temperature environment.

Example 14: Solid Soap

TABLE 11

| <Components> | Weight (%) |
|---|---|
| 1. Fatty acid alkali metal salt (lauric acid 38%, myristic acid 37%, palmitic acid 15%, stearic acid 10%) (potassium:sodium = 1:5) | 94.5 |
| 2. Cocamidopropyl betaine | 3.0 |
| 3. Glycerine | 2.0 |
| 4. Production Example 2 (Sample B) black iron oxide with a high tinting strength | 0.5 |

<Production Method>
A: Sodium hydroxide (48%) and potassium hydroxide (48%) were added to a fatty acid of a composition of Component 1, then the mixture was stirred/mixed at a high temperature to prepare a fatty acid alkali metal salt of Component 1.
B: Components 2 to 4 were added to A, and mixed together, then the mixture was homogenized using a three roll mill.
C: B was kneaded/pressurized and extruded into a stick soap with an extruder, then molded with a stamping machine to obtain a solid soap.

The obtained solid soap had a water content of 11.5%, and it had a stable blackness and somewhat of a red tint.

Example 15: Bath Powder

TABLE 12

| <Components> | Weight (%) |
|---|---|
| 1. Sodium sulfate | 86.0 |
| 2. Sodium hydrogen carbonate | residue |
| 3. Sodium glutamate | 2.0 |
| 4. Silica (AGC Si-Tech Co., Ltd. SUNSPHERE H-52) | 1.0 |
| 5. Production Example 1 (Sample A) black iron oxide with a high tinting strength | 0.5 |
| 6. Vanillylbutyl ether | 0.2 |
| 7. Capsicum extract | 0.1 |

<Production Method>
Components 1 to 7 were weighed out and mixed evenly using a Henschel mixer to obtain a bath powder.

A use of the obtained bath powder made the warm water in the bath tub turn a translucent black color.

Example 16: Peel-Off Mask

TABLE 13

| <Components> | Weight (%) |
|---|---|
| 1. PEG1500 | 8.0 |
| 2. PEG/PPG-25/30 copolymer | 6.0 |
| 3. Xanthan gum | 0.2 |
| 4. Sodium citrate | 0.3 |
| 5. Citric acid | 0.1 |
| 6. Purified water | 49.0 |
| 7. Polyvinyl alcohol | 10.0 |
| 8. Polysorbate-80 | 0.2 |
| 9. Silica (AGC Si-Tech Co., Ltd. SUNSPHERE H-51) | 4.0 |
| 10. Talc | 8.0 |
| 11. Production Example 1 (Sample A) black iron oxide with a high tinting strength | 1.0 |

TABLE 13-continued

| <Components> | Weight (%) |
|---|---|
| 12. Alkyl acrylate copolymer emulsion | 5.0 |
| 13. Methylparaben | 0.2 |
| 14. Ethanol | 8.0 |

<Production Method>
A: Components 9 to 11 were mixed/ground.
B: To heated/dissolved Components 1 to 8, A was added and evenly dispersed, then, the mixture was cooled to 40° C.
C: Components 12 to 14 were added to B, then stirred/cooled to room temperature to prepare a peel-off mask.

The obtained peel-off mask exhibited a homogenous black color, and it made sebum and dirt visible after the mask was removed.

What is claimed is:

1. A method, comprising:
reacting a ferrous salt solution with an alkali hydroxide to form a ferrous hydroxide slurry;
adding a ferric salt solution to the ferrous hydroxide slurry to produce a ferrous hydroxide slurry comprising a nucleus of black iron oxide;
adjusting a pH of the ferrous hydroxide slurry comprising the nucleus of black iron oxide to 12.0 to 13.0;
introducing an oxygen-containing gas over the ferrous hydroxide slurry comprising the nucleus of black iron oxide and heating the slurry to grow the nucleus of black iron oxide and form a slurry comprising a black iron oxide particle; and
adding an inorganic metal salt to the slurry comprising the black iron oxide particle to foiln a black iron oxide particle having a layer comprising a hydroxide or an oxide of the inorganic metal salt coated on a surface thereof and having an octahedral shape and a specific surface area of 8.0 to 20.0 $m^2/g$,
wherein an L*value of a colour on reduction of the black iron oxide particle having a layer containing an hydroxide or an oxide of the inorganic metal salt on a surface thereof according to JIS K5101-3-1 is 31.0 or lower and a b*value of a colour on reduction of the black iron oxide particle having a layer containing a hydroxide or an oxide of the inorganic metal salt on a surface thereof according to JIS K5101-3-1 is 1.5 or lower.

2. The method according to claim 1, wherein the hydroxide or oxide of the inorganic metal salt coated on the surface of the black iron oxide particle is a hydroxide or an oxide of one or more of aluminum, silicon, zinc, titanium, zirconium, cerium, or tin.

3. The method according to claim 1, further comprising incorporating the black iron oxide particle having a layer containing a hydroxide or an oxide of the inorganic metal salt on a surface thereof into a cosmetic material.

4. The method according to claim 3, wherein the cosmetic material is in the form of a makeup base, foundation, concealer, face powder, control color, sun screen, lipstick, lip cream, eye shadow, eye liner, mascara, cheek color, manicure, body powder, perfume powder, baby powder, solid soap, bath powder, or peel-off mask.

5. The method according to claim 1, wherein the ferric salt is selected from ferric chloride, ferric sulfate, and ferric nitrate.

6. The method according to claim 1, wherein the ferric salt solution is added to the slurry in an amount of 0.8 to 5.0 wt % as $Fe^{3+}$ against 100 wt % of $Fe^{2+}$.

7. The method according to claim 1, wherein the inorganic metal salt is added to the slurry containing the black iron oxide particle in an amount that can form the layer containing the hydroxide or the oxide of the inorganic metal salt in an amount of 0.5 to 5.0 wt % against 100 wt % of the black iron oxide particle.

* * * * *